US012734356B2

(12) United States Patent
Jin et al.

(10) Patent No.: US 12,734,356 B2
(45) Date of Patent: Sep. 15, 2026

(54) LEAD FOR PACING

(71) Applicant: Kossel Medtech (Suzhou) Co., Ltd., Suzhou (CN)

(72) Inventors: Han Jin, Beijing (CN); Yiran Hu, Beijing (CN)

(73) Assignee: Kossel Medtech (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 18/996,355

(22) PCT Filed: Oct. 26, 2023

(86) PCT No.: PCT/CN2023/126898

§ 371 (c)(1), (2) Date: Jan. 17, 2025

(87) PCT Pub. No.: WO2025/055063

PCT Pub. Date: Mar. 20, 2025

(65) Prior Publication Data

US 2026/0007879 A1 Jan. 8, 2026

(30) Foreign Application Priority Data

Sep. 13, 2023 (CN) ........................ 202311176062.3

(51) Int. Cl.
*A61N 1/05* (2006.01)
*A61N 1/362* (2006.01)

(52) U.S. Cl.
CPC ......... *A61N 1/0573* (2013.01); *A61N 1/0565* (2013.01); *A61N 1/362* (2013.01)

(58) Field of Classification Search
CPC .... A61N 1/0573; A61N 1/0575; A61N 1/057; A61N 1/0565; A61N 1/059

(Continued)

(56) References Cited

U.S. PATENT DOCUMENTS 4,475,560 A 10/1984 Tarjan et al.
6,459,937 B1 10/2002 Morgan et al.
(Continued)

FOREIGN PATENT DOCUMENTS

CN 103384546 A 11/2013
CN 204601383 U 9/2015
(Continued)

OTHER PUBLICATIONS

International Search Report cited in PCT/CN2023/126898, mailed Jun. 7, 2024, 12 pages.

(Continued)

*Primary Examiner* — George R Evanisko
(74) *Attorney, Agent, or Firm* — Cooper Legal Group, LLC

(57) ABSTRACT

The present application relates to a lead for pacing, including: an insulating layer, an electrode head, and at least one anchoring member, where the electrode head is movable relative to the insulating layer between a first position and a second position; the at least one anchoring member is movable relative to the insulating layer between a third position and a fourth position, where the first position is closer to a proximal end of the lead than the second position; the third position is closer to the proximal end of the lead than the fourth position; the electrode head in the first position and the at least one anchoring member in the third position are located within the insulating layer, where an electrode extension portion is a part of the electrode head extending out of the insulating layer.

6 Claims, 8 Drawing Sheets

(58) Field of Classification Search
USPC .......................................................... 607/128
See application file for complete search history.

(56) References Cited

U.S. PATENT DOCUMENTS

| | | | | |
|---|---|---|---|---|
| 11,666,752 | B2 * | 6/2023 | Haasl ................. | A61N 1/37518 607/128 |
| 11,712,188 | B2 | 8/2023 | Ghosh | |
| 2006/0009827 | A1 | 1/2006 | Kurth | |
| 2018/0264272 | A1 | 9/2018 | Haasl et al. | |
| 2019/0269929 | A1 | 9/2019 | Bjorklund et al. | |
| 2020/0197693 | A1 | 6/2020 | Liu et al. | |
| 2023/0201579 | A1 | 6/2023 | Regnier et al. | |

FOREIGN PATENT DOCUMENTS

| | | | |
|---|---|---|---|
| CN | 109529194 | A | 3/2019 |
| CN | 111437512 | A | 7/2020 |
| CN | 111991696 | A | 11/2020 |
| CN | 113289244 | A | 8/2021 |
| CN | 115869542 | A | 3/2023 |
| CN | 116053825 | A | 5/2023 |
| CN | 116392716 | A | 7/2023 |
| CN | 116920279 | A1 | 10/2023 |
| WO | 2023144544 | A | 8/2023 |

OTHER PUBLICATIONS

Written Opinion cited in PCT/CN2023/126898, mailed Jun. 7, 2024, 17 pages.
First CN Office Action cited in CN202311176062.3, mailed Oct. 30, 2023, 9 pages.
Notification of Grant cited in CN202311176062.3, mailed Nov. 16, 2023, 14 pages.

* cited by examiner

LEAD FOR PACING

CROSS-REFERENCE TO RELATED APPLICATION

This application claims priority to Chinese Patent Application No. 202311176062.3 filed with the China National Intellectual Property Administration on Sep. 13, 2023, and entitled "LEAD FOR PACING", which is incorporated herein by reference in its entirety.

FIELD

The present application relates to the technical field of implantable medical devices, and particularly to a lead for pacing applied to the left bundle branch area of the heart.

BACKGROUND

Implanting a permanent cardiac pacemaker is an effective and mature technical means for treating arrhythmias. Typically, a cardiac pacing lead is implanted into the myocardial tissue at the right ventricular apex or septum to deliver electrical pulses for local myocardial pacing. However, over the years of clinical practice, it has been found that this traditional method of pacing the right ventricular myocardium may cause electrical desynchronization between the left and right ventricles, thereby increasing the risk of long-term chronic heart failure or atrial fibrillation in patients. In 2017, researchers first passed the cardiac pacing lead through the interventricular septum, directly pacing the subendocardial left bundle branch conduction system of the left ventricle (rather than just acting on the myocardial tissue), thus achieving physiological left bundle branch area pacing (LBBAP) for the first time. This pacing method can ensure that electrical pulses directly pace the heart's normal electrical conduction system, allowing for synchronized contraction of the left ventricle. It is currently considered the most feasible, promising, and effective physiological pacing method. Currently, the cardiac pacing leads available for the LBBAP in clinical practice are mainly divided into two categories: (1) the spiral active lead (model: 3830) produced by Medtronic, which serves as a solid cardiac active pacing lead. Its main design features are: a, a small diameter of only 1.4 mm; b, completely solid with no internal steel wire support; and c, a completely exposed spiral head. However, this design encounters two problems when implementing the LBBAP: 1) difficulty in screwing the pacing lead into the left bundle branch area deep in the interventricular septum: due to being completely solid with no internal steel wire support, the lead is relatively soft overall, and the myocardium wrapped around the spiral inside may obstruct the lead's advance into the deeper septal myocardium; 2) difficulty in long-term removal: cardiac pacing leads are typically used for 10-15 years, and during this time, if the patient experiences infections, lead failures, and other uncontrollable factors, lead removal is required. However, since the lead head is completely screwed deep into the interventricular septum, the design of the spiral head, while ensuring a secure connection of the lead, also brings the problem of repeated winding of the surrounding myocardium and fibrous tissue with the spiral steel wire, making the removal of this spiral active lead implanted in the left bundle branch area exceedingly difficult.

In addition, the above-mentioned commercially available cardiac pacing leads are not specifically designed and developed for the LBBAP. There are currently related arts that disclose new pacing lead designs that can be used for the LBBAP, including the following patent applications. a, Chinese patent application with publication number CN113289244A discloses a quadrupole spiral active lead for pace-making of a His Purkinje System. However, the design of the spiral head still cannot solve the problem of the difficulty in long-term removal. Furthermore, the quadrupole spiral active lead provides a plurality of ring electrodes for pacing so that it is incompatible with the currently available pulse generators. Thus, it is necessary to simultaneously develop a matched special pulse generator. b, Chinese patent application with publication number CN116053825A discloses an implantable lead connector, which likewise cannot solve the problem of the difficulty in long-term removal. c, Chinese patent publication with publication number CN116392716A discloses a biostimulator for a pacing element for deep interval pacing. The device is designed for the direct implantation of a leadless pacemaker into the myocardium and is not a single pacing lead. In addition, the head of this device is sharp and directly exposed, so it is necessary to develop a matched special delivery sheath. Otherwise, it will puncture the myocardium or blood vessel. d, US patent publication with publication number U.S. Pat. No. 11,712,188B2 discloses posterior left bundle branch engagement, in which after the fixation member (20) penetrates the heart tissue to a certain depth, it is reversely bent to grab the heart tissue in a claw-like manner, thereby fixing the device at the heart tissue. The fixation manner of the structure may cause great damage and potential burden to the heart tissue, and may also cause difficulty for the physician to remove the lead from the heart tissue.

SUMMARY

In order to overcome at least one of the defects described in the above related art, it is an object of the present application to provide a lead for pacing that facilitates removal by a physician.

The lead for pacing provided by the present application includes: an insulating layer, an electrode head, and at least one anchoring member, where the electrode head is movable relative to the insulating layer between a first position and a second position; the at least one anchoring member is movable relative to the insulating layer between a third position and a fourth position, where the first position is closer to a proximal end of the lead than the second position; the third position is closer to the proximal end of the lead than the fourth position;

the electrode head in the first position and the at least one anchoring member in the third position are located within the insulating layer; the electrode head in the second position partially or completely extends out of the insulating layer; the at least one anchoring member in the fourth position partially or completely extends out of the insulating layer; a cross section of an electrode extension portion of the electrode head does not increase from a proximal end to a distal end along an axial direction of the electrode head, and a cross section of a member extension portion of the at least one anchoring member does not increase from a proximal end to a distal end along an axial direction of the anchoring member, where the electrode extension portion is a part of the electrode head extending out of the insulating layer, and the member extension portion is a part of the anchoring member extending out of the insulating layer.

In some embodiments, the electrode head includes a first cylindrical portion and a first tapered head connected sequentially from the proximal end to the distal end along the axial direction of the electrode head, or the electrode head is tapered;

the anchoring member includes a second cylindrical portion and a second tapered head connected sequentially from the proximal end to the distal end along the axial direction of the anchoring member, or the anchoring member is tapered.

In some embodiments, the lead for pacing further includes a first pushing rod and a movable portion, where the first pushing rod is fixedly connected to the electrode head; the movable portion is formed with a first through hole for the first pushing rod to pass through, and the first pushing rod and the first through hole are in interference connection; the at least one anchoring member is mounted on the movable portion, where the movable portion is movably mounted in the insulating layer; pushing the first pushing rod is able to drive the movable portion to move, thereby driving the at least one anchoring member to move.

In some embodiments, when pushing the first pushing rod to move distally to drive the electrode head to move from the first position to the second position and drive the at least one anchoring member to move from the third position to the fourth position, the at least one anchoring member extends out of the insulating layer before the electrode head extends out of the insulating layer.

In some embodiments, the lead further includes a second pushing rod and an electrode rod, where a distal end of the electrode rod is fixedly connected to the electrode head; the second pushing rod is formed with a second through hole; the electrode rod passes through the second through hole, and the electrode rod and the second through hole are in interference connection; the at least one anchoring member is connected to a distal end of the second pushing rod through a deformable piece, where a limiting channel is formed in the insulating layer for the deformable piece to pass through and limits the position of the deformable piece.

In some embodiments, when pushing the second pushing rod to move distally to drive the electrode head to move from the first position to the second position and drive the at least one anchoring member to move from the third position to the fourth position through the deformable piece, the at least one anchoring member extends out of the insulating layer before the electrode head extends out of the insulating layer.

In some embodiments, a restraining piece is provided in the insulating layer; when pushing the second pushing rod and the deformable piece to drive the at least one anchoring member to move from the third position to the fourth position, the restraining piece restrains the second pushing rod to move distally.

In some embodiments, the second pushing rod extends proximally out of the insulating layer, and a proximal end of the electrode rod is provided with graduated markers.

In some embodiments, the deformable piece is movable and deformable along the limiting channel under the action of an external force.

In some embodiments, the insulating layer is arranged with an annular groove formed by recessing inwardly, and the annular groove circumferentially surrounds the insulating layer.

In some embodiments, the at least one anchoring member includes three anchoring members.

In some embodiments, the insulating layer is formed with a first cathode interface, a second cathode interface, a first anode interface, and a second anode interface, where the first cathode interface and the second cathode interface are communicated with each other, and the first anode interface and the second anode interface are communicated with each other.

In some embodiments, the at least one anchoring member is configured to fix the lead for pacing to heart tissue; the at least one anchoring member is inserted into the heart tissue when the at least one anchoring member is in the fourth position; the at least one anchoring member does not hook the heart tissue when the at least one anchoring member moves from the fourth position to the third position; the electrode head is inserted into the heart tissue when the electrode head is in the second position; the electrode head does not hook the heart tissue when the electrode head moves from the second position to the first position.

According to the lead for pacing of the present application, at least one anchoring member is provided so that the lead may be stably fixed in the heart. Meanwhile, since the electrode extension portion of the electrode head and the member extension portion of the anchoring member do not increase from the proximal end to the distal end, it is not easy to hook the heart tissue, so as to facilitate the later removal of the electrode head and the anchoring member from the heart.

BRIEF DESCRIPTION OF THE DRAWINGS

In order to more clearly illustrate the technical solutions in the embodiments of the present application, the drawings required in the descriptions of the embodiments will be briefly introduced below. Obviously, the drawings described below are only some embodiments of the present application, and a person skilled in the art may obtain other drawings according to these drawings without involving any inventive effort.

FIG. 5*a* shows a state where an electrode head and an anchoring member are not extended out of the insulating layer, FIG. 5*b* shows a state where the anchoring member is in a fourth position, and FIG. 5*c* shows a state where the electrode head is in a second position;

FIG. 6 shows a state where an anchoring member is in a fourth position and an electrode head is in a second position; FIG. 7 shows a state where the anchoring member is in a fourth position; FIG. 8 shows a state where the anchoring member is in the third position and the electrode head is in the first position;

FIG. 9*a* shows a state where an electrode head and an anchoring member are not extended out of the insulating layer, FIG. 9*b* shows a state where the anchoring member is in a fourth position, and FIG. 9*c* shows a state where the electrode head is in a second position;

DETAILED DESCRIPTION

Figure 1:
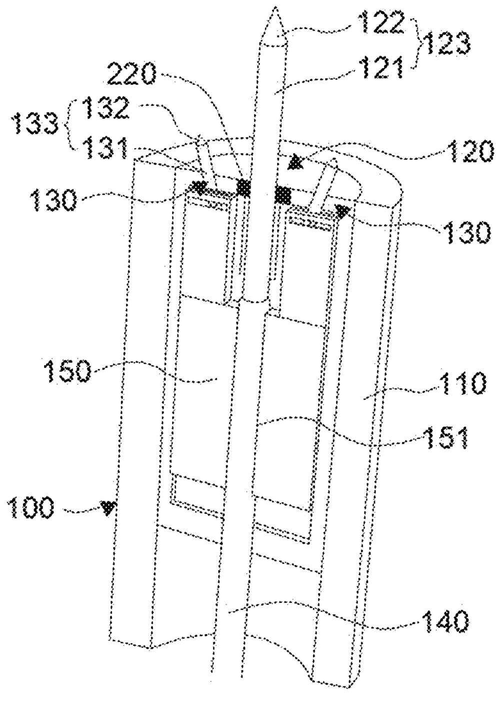
FIG. 1 is a perspective view of a lead for pacing according to some embodiments of the present application, where the lead is sectioned along either axial section.

In order to make the object, technical solutions, and advantages of the present application clearer, the technical solutions in the embodiments of the present application will be clearly and completely described below in conjunction with the accompanying drawings in the embodiments of the present application. Obviously, the described embodiments are only some embodiments of the present application, not all embodiments. Based on the embodiments of the present application, all other embodiments obtained by a person skilled in the art without inventive effort fall within the scope of the present application.

In the description of the present application, it should be understood that orientation or positional relationships indicated by the terms "X-axis", "Y-axis", "Z-axis", "vertical", "parallel", "upper", "lower", "front", "back", "left", "right", "vertical", "horizontal", "top", "bottom", "inner", "outer", and the like are based on the orientation or positional relationships shown in the drawings, are intended only to facilitate and simplify the description of the present application, and are not intended to indicate or imply that the apparatus or element referred to must have a particular orientation, constructed and operated in a particular orientation, and therefore are not to be construed as limitations of the present application. In addition, the terms "first" and "second" are used for descriptive purposes only and are not to be construed as indicating or implying relative importance or implicitly indicating the number of technical features indicated. Thus, a feature defined as "first" or "second" may explicitly or implicitly include one or more such features. In the description of the present application, unless otherwise indicated, the meaning of "a plurality of" means two or more.

In the description of the present application, it should be noted that, unless otherwise explicitly stated or limited, the terms "mounted", "communicated", and "connected" are to be construed broadly, such as fixedly connected, detachably connected, integrally connected, mechanically connected, electrically connected, directly connected, indirectly connected through an intermediate medium, and communicated between two elements. The specific meanings of the above-mentioned terms in the present application may be understood by a person skilled in the art according to specific circumstances.

Figure 2:
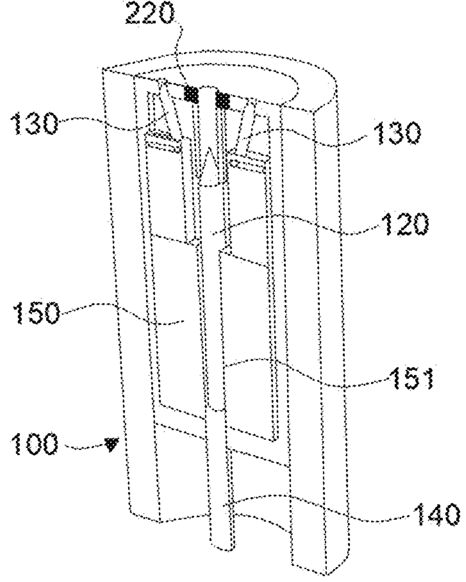
FIG. 2 is a perspective view of the lead of the embodiment shown in FIG. 1 in a state where an electrode head and an anchoring member are not extended.

FIG. 1 is a perspective view of a lead for pacing according to one embodiment of the present application, where the lead is sectioned along an axial section. FIG. 2 is a perspective view of the lead of the embodiment shown in FIG. 1 in a state where an electrode head and an anchoring member have not extended out of the insulating layer. As shown in FIGS. 1 and 2, a lead 100 includes an insulating layer 110, an electrode head 120, and at least one anchoring member 130. The electrode head 120 is movable relative to the insulating layer 110 between a first position (i.e., its retracted position) and a second position (i.e., its fully extended position). The anchoring member 130 is movable relative to the insulating layer 110 between a third position (i.e., its retracted position) and a fourth position (i.e., its fully extended position). It is contemplated that when the electrode head 120 is in the first position and the anchoring member 130 is in the third position, they are closer to a proximal end of the lead 100 (than in the second position and the fourth position). In addition, when the electrode head 120 is in the first position and the anchoring member 130 is in the third position, both the electrode head 120 and the anchoring member 130 are located within the insulating layer 110, particularly within a channel for which the insulating layer 110 is specially configured, as shown in FIG. 2. When the electrode head 120 is in the second position and the anchoring member 130 is in the fourth position, they are closer to a distal end of the lead 100 (than in the first position and the third position), as shown in FIG. 1.

Figures 3, 4:
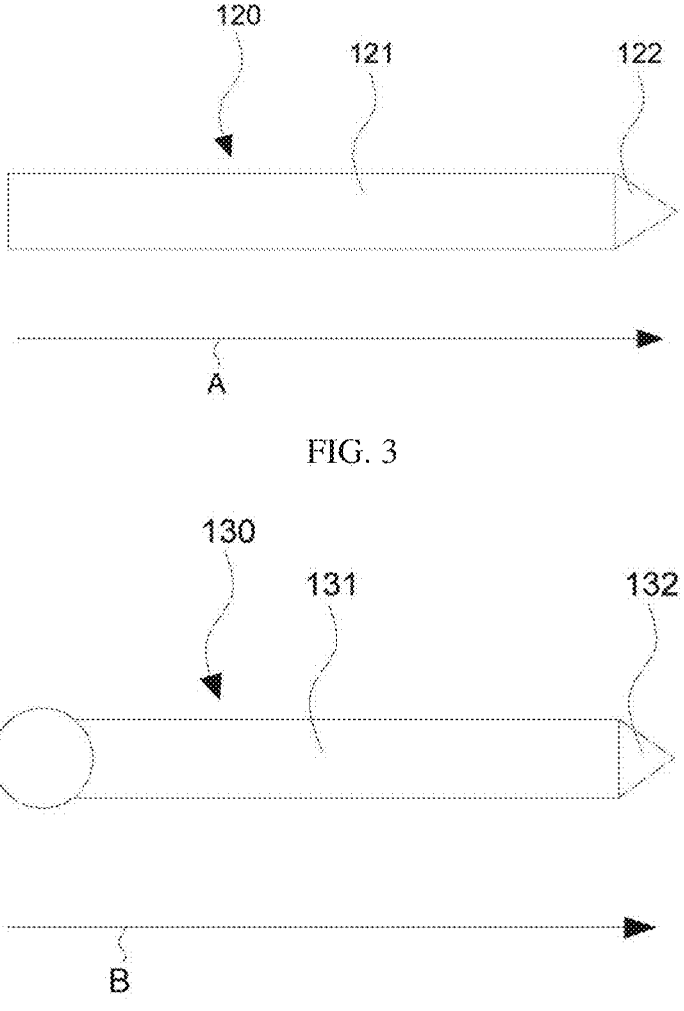
FIG. 3 is a schematic structural diagram of an electrode head of the embodiment shown in FIG. 1.
FIG. 4 is a schematic structural diagram of an anchoring member of the embodiment shown in FIG. 1.

As shown in FIG. 3, the electrode head 120 may be designed to include a first cylindrical portion 121 and a first tapered head 122 connected sequentially from the proximal end to the distal end along an axial direction A of the electrode head 120. In some embodiments, the electrode head 120 may take the form of a cone. Similarly, as shown in FIG. 4, the anchoring member 130 may be designed to include a second cylindrical portion 131 and a second tapered head 132 connected sequentially from the proximal end to the distal end along the axial direction B of the anchoring member 130. In some embodiments, the anchoring member 130 may take the form of a cone. This means that the electrode head 120 and the anchoring member 130 do not have a smaller cross section near their axial proximal ends than near their distal ends. This also makes a cross section of a part of the electrode head 120 extending out of the insulating layer in the above-mentioned solution, in some embodiments, an electrode extension portion 123, not increase from the proximal end to the distal end along the axial direction A of the electrode extension portion 123, and makes a cross section of a part of the anchoring member 130 extending out of the insulating layer 110 in the above-mentioned solution, in some embodiments, a member extension portion 133, not increase from the proximal end to the distal end along the axial direction B of the member extension portion 133. In some embodiments, when an interventional physician proximally moves the anchoring member 130 and the electrode head 120 to retract into the insulating layer 110 (in some embodiments, moves the anchoring member 130 from the fourth position to the third position and moves the electrode head 120 from the second position to the first position), neither the electrode head 120 nor the anchoring member 130 hooks the heart tissue, thereby preventing significant damage to the heart tissue.

It should be noted that the electrode head 120 and the anchoring member 130 are made of a hard material, which is not easily deformed, and may be a metal or an alloy.

The lead 100 further includes a first pushing rod 140 and a movable portion 150. The first pushing rod 140 is fixedly connected to the electrode head 120. The movable portion 150 is arranged with a first through hole 151 through which the first pushing rod 140 extends. In some embodiments, the first pushing rod 140 is in an interference fit with the first through hole 151. The anchoring member 130 is mounted on the movable portion 150. It should be noted that the insulating layer 110 is formed with a limiting cavity for limiting the movable portion 150. In addition, a part of the first pushing rod 140 located in the first through hole 151 is provided with a rubber sleeve. The rubber sleeve (not shown in the drawings) sleeves the first pushing rod 140 so that the first pushing rod 140 is in an interference fit with the first through hole 151.

In some embodiments, the anchoring member 130 is movably mounted on the movable portion 150. In some embodiments, the movable portion 150 is formed with a movable cavity along which the proximal portion of the anchoring member 130 is constrained to move only. In some embodiments, the proximal portion of the anchoring member 130 is inserted into a limiting groove (not shown in the drawings) of the movable cavity so that the proximal portion of the anchoring member 130 can only move along the limiting groove of the movable cavity. In the above-mentioned solution, the anchoring member 130 is movably mounted on the movable portion 150 so that the position and orientation of the anchoring member 130 may be changed during the pushing process, thereby facilitating the extension of the anchoring member 130 from the insulating layer 110. In some embodiments, the size of the through hole in the insulating layer 110 through which the anchoring member 130 passes may also be adjusted to facilitate the passage of the anchoring member 130.

It should be noted that the distal end of the insulating layer 110 is arranged with a second cathode interface 220, a specific structure of which will be described later in the description.

Figures 5A, 5B:
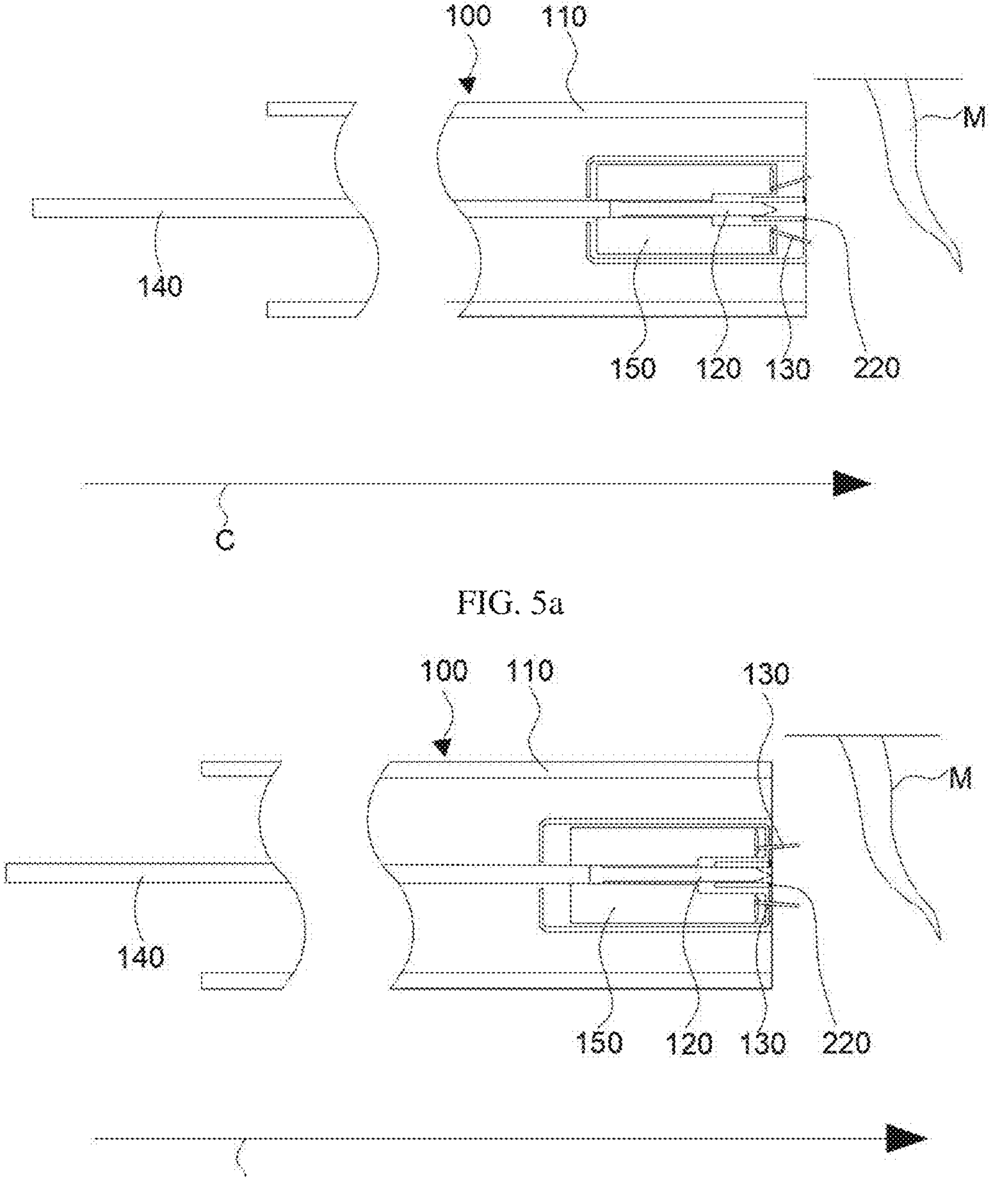
FIGS. 5*a-c* are cross-sectional views of the lead of the embodiment shown in FIG. 1 in different states, where
Figure 5C:
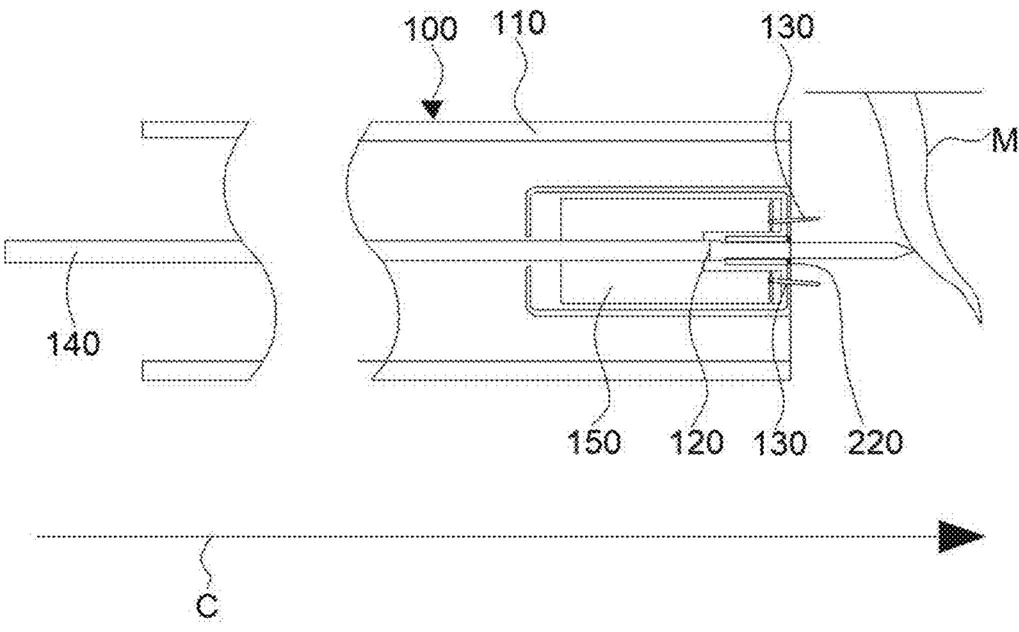

FIGS. 5*a-c* are cross-sectional views of the lead of the embodiment shown in FIG. 1 in different states, where FIG. 5*a* shows a state where the electrode head and the anchoring member are not extended out of the insulating layer, FIG. 5*b* shows a state where the anchoring member is in the fourth position, and FIG. 5*c* shows a state where the electrode head is in the second position. Referring to FIG. 5*a*, at the beginning of implanting the lead 100, the electrode head 120 is in the first position, and the anchoring member 130 is in the third position. At this time, the interventional physician pushes the first pushing rod 140 to move distally, thereby driving the electrode head 120 to move from the first position to the second position, and driving the anchoring member 130 to move from the third position to the fourth position due to the interference fit of the first pushing rod 140 with the first through hole 151. It should be noted that although the electrode head 120 and the anchoring member 130 are moved distally at the same time, the anchoring member 130 extends out of the insulating layer and is in the fourth position before the electrode head 120 extends out of the insulating layer, thereby anchoring the lead 100 within the myocardium, as shown in FIG. 5*b*. At this time, the interventional physician needs to apply more force to push the first pushing rod 140 to continue moving distally, and may even incorporate a rotation operation while pushing, allowing the first pushing rod 140 to be screwed further distally. Thus, in the case where the movable portion 150 has been constrained by the limiting cavity (not shown in the drawings), resulting in the anchoring member 130 being constrained in the fourth position, the first pushing rod 140 continues to push the electrode head 120 to the second position, slightly piercing the left bundle branch area M in the myocardium, as shown in FIG. 5*c*. In the above-mentioned solution, the anchoring member 130 extends out of the insulating layer before the electrode head 120 extends out of the insulating layer to ensure that the anchoring member 130 may be inserted into the left bundle branch area M for anchoring, thereby facilitating the subsequent slow and accurate insertion of the electrode head 120 into the myocardial tissue. It should be noted that a direction C is the axial direction of the lead.

When removal of the lead 100 is required, the interventional physician may pull the first pushing rod 140 to move proximally while driving the electrode head 120 to move proximally. At this time, due to the interference fit of the first pushing rod 140 with the first through hole 151, the movable portion 150 and the anchoring member 130 may also move proximally from the fourth position to the third position. When the anchoring member 130 is in the third position, the movable portion 150 and the anchoring member 130 can no longer move proximally due to the restriction of the limiting cavity. The interventional physician may pull the first pushing rod 140 while incorporating a rotation operation so that the first pushing rod 140 can be screwed proximally.

Figure 6:
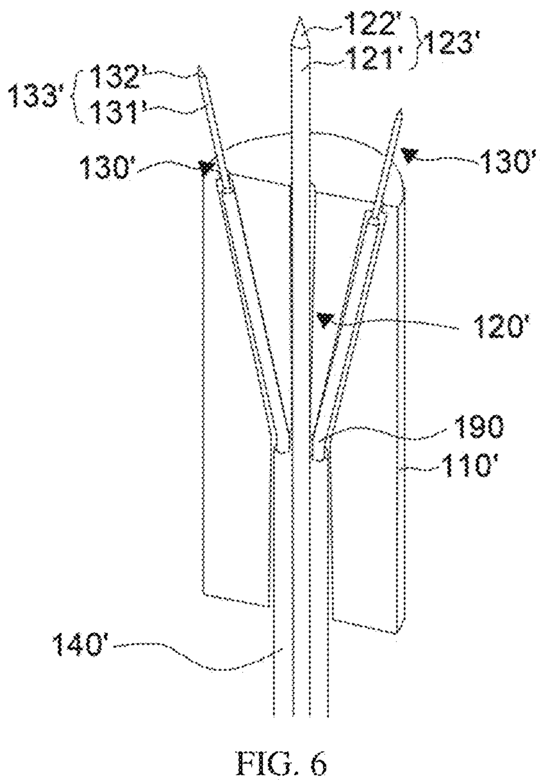
FIGS. 6-8 are perspective views of a lead for pacing in different states according to another embodiment of the present application, where the lead is sectioned along an axial section, where
Figure 7:
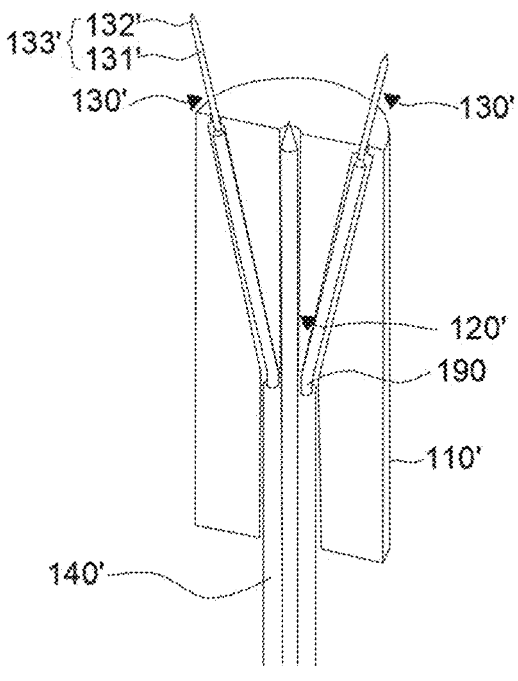
Figure 8:
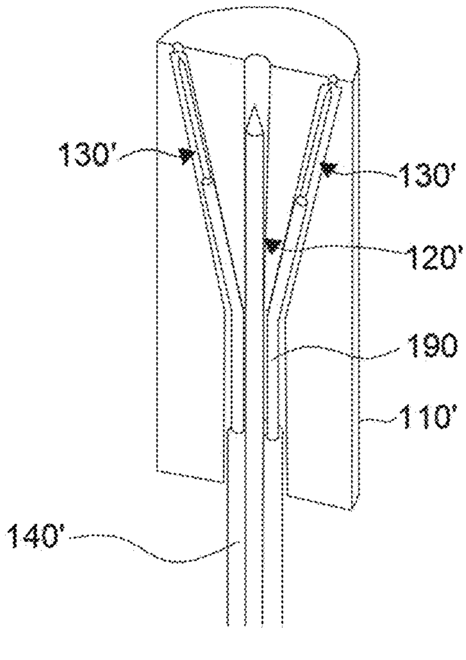

FIGS. 6-8 are perspective views of a lead for pacing in different states according to another embodiment of the present application, where the lead is sectioned along an axial section. FIG. 6 shows a state where an anchoring member is in a fourth position and an electrode head is in a second position. FIG. 7 shows a state where the anchoring member is in a fourth position. FIG. 8 shows a state where the anchoring member is in the third position and the electrode head is in the first position. The lead 100' includes an insulating layer 110', an electrode head 120', and at least one anchoring member 130'. The electrode head 120' is movable relative to the insulating layer 110' between a first position (in some embodiments, the first position is its retracted position) and a second position (in some embodiments, the second position is its fully extended position). The anchoring member 130' is movable relative to the insulating layer 110' between a third position (in some embodiments, the third position is its retracted position) and a fourth position (in some embodiments, the fourth position is its fully extended position). It is contemplated that when the electrode head 120' is in the first position and the anchoring member 130' is in the third position, they are closer to a proximal end of the lead 100' (than in the second position and the fourth position). In addition, when the electrode head 120' is in the first position and the anchoring member 130' is in the third position, both the electrode head 120' and the anchoring member 130' are located within the insulating layer 110', particularly within a channel for which the insulating layer 110' is specially configured.

The electrode head 120' may be designed to include a first cylindrical portion 121' and a first tapered head 122' connected sequentially from the proximal end to the distal end along an axial direction of the electrode head 120'. In some embodiments, the electrode head 120' may take the form of a cone. Similarly, the anchoring member 130' may be designed to include a second cylindrical portion 131' and a second tapered head 132' connected sequentially from the proximal end to the distal end along the axial direction of the anchoring member 130'. In some embodiments, the anchoring member 130' may take the form of a cone. This means that the electrode head 120' and the anchoring member 130' do not have a smaller cross section near their proximal ends than near their distal ends. This makes a cross section of a part of the electrode head 120' extending out of the insulating layer in the above-mentioned solution, for example, an electrode extension portion 123', not increase from the proximal end to the distal end along the axial direction of the electrode head 120', and makes a cross section of a part of the anchoring member 130' extending out of the insulating layer in the above-mentioned solution, for example, a member extension portion 133', not increase from the proximal end to the distal end along the axial direction of the anchoring member 130'. In some embodiments, when an interventional physician proximally moves the anchoring member 130' and the electrode head 120' to retract into the insulating layer 110'. In some embodiments, it means that the interventional physician moves the anchoring member

130' from the fourth position to the third position and moves the electrode head 120' from the second position to the first position, neither the electrode head 120' nor the anchoring member 130' hooks the heart tissue, thereby preventing significant damage to the heart tissue.

It should be noted that the electrode head 120' and the anchoring member 130' are made of a hard material, which is not easily deformed, and may be a metal or an alloy.

The lead 100' further includes a second pushing rod 140' and an electrode rod 160, and a distal end of the electrode rod 160 is fixedly connected to the electrode head 120'. The second pushing rod 140' is arranged with a second through hole through which the electrode rod 160 extends. In some embodiments, the electrode rod 160 is in an interference fit with the second through hole. The anchoring member 130' is indirectly connected to the second pushing rod 140' through a deformable piece 190. In some embodiments, a distal end of the second pushing rod 140' is fixedly connected to the deformable piece 190, and a distal end of the deformable piece 190 is fixedly connected to the anchoring member 130'. It is contemplated that the deformable piece 190 is also located within the insulating layer 110', within a limiting channel 112 for which the insulating layer 110' is specially configured. The deformable piece 190 is made of a memory metal, such as nickel alloy or titanium alloy. The deformable piece 190 is movable and deformable along the limiting channel 112 under the action of an external force. It should be noted that a rubber sleeve (not shown in the drawings) is provided outside the electrode rod 160 so that the electrode rod 160 is in an interference fit with the second through hole. In addition, in some embodiments, the electrode rod 160 may be integrally formed with the electrode head 120'.

Figure 9A:
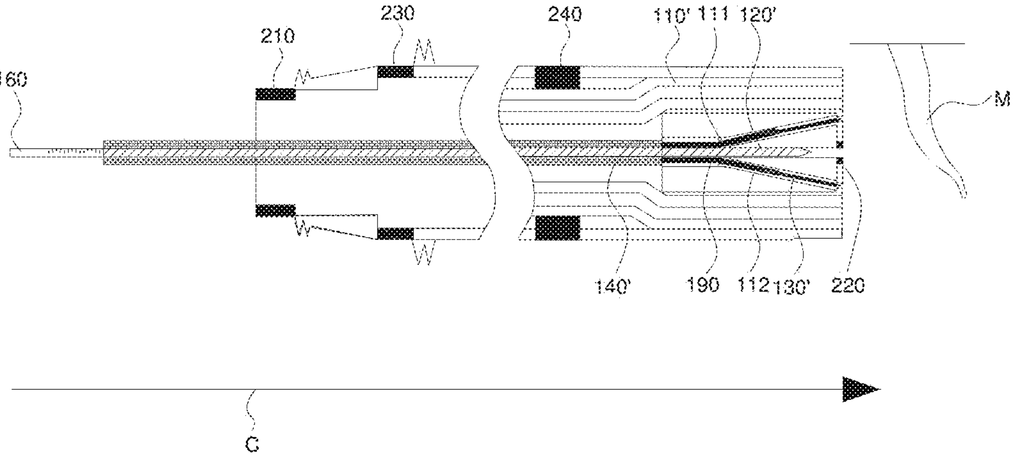
FIGS. 9*a-c* are cross-sectional views of the lead of the embodiment shown in FIG. 6 in different states, where
Figure 9B:
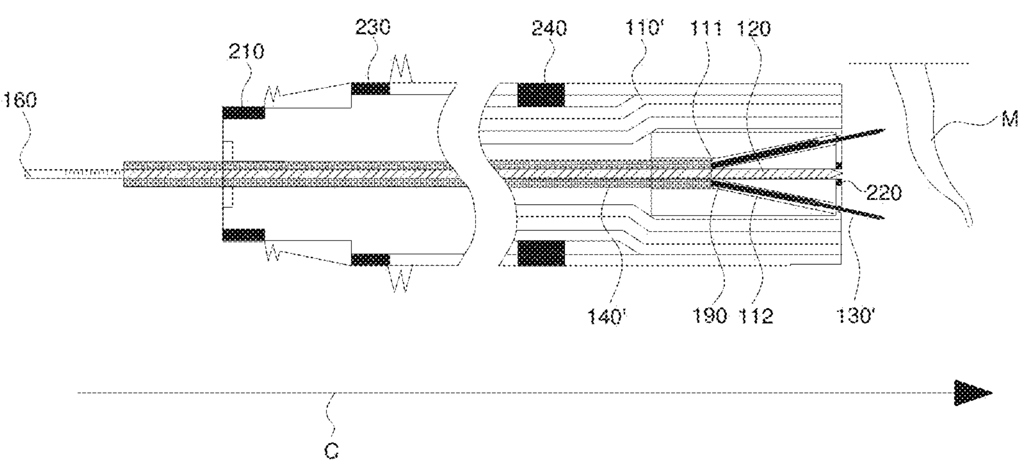
Figure 9C:
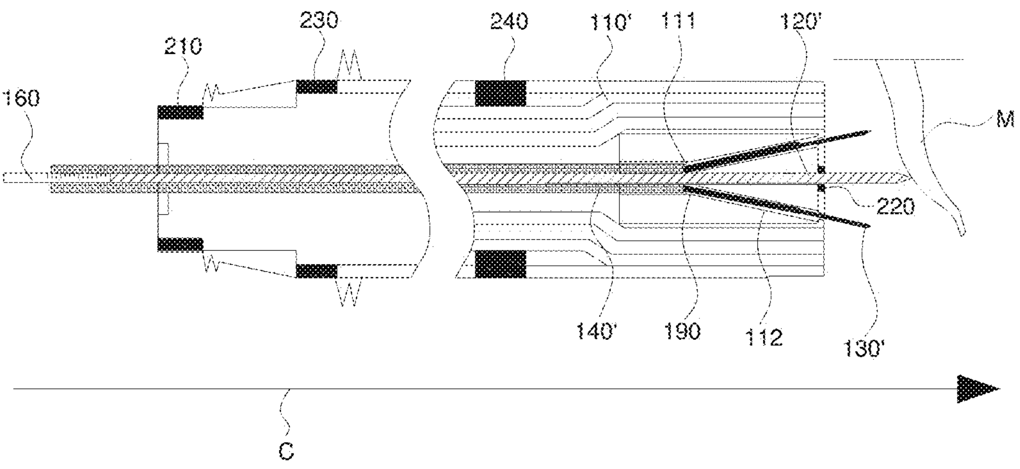

As shown in FIG. 9*a*, at the beginning of implanting the lead 100', the electrode head 120' is in the first position, and the anchoring member 130' is in the third position. The interventional physician pushes the second pushing rod 140' to move distally, so as to drive the electrode rod 160 to move through the interference fit of the electrode rod 160 with the second through hole, thereby driving the electrode head 120' on the electrode rod 160 to move from the first position to the second position. In addition, the distal end of the second pushing rod 140' may also drive the deformable piece 190 to move, thereby driving the anchoring member 130' to move from the third position to the fourth position. It should be noted that although the electrode head 120' and the anchoring member 130' are moved distally at the same time, the anchoring member 130' reaches the fourth position before the electrode head 120' so that the lead 100' may be anchored to the left bundle branch area M first through the anchoring member 130', as shown in FIG. 9*b*. At this time, the second pushing rod 140' is restrained from further forward movement by a restraining piece 111, thereby restraining the anchoring member 130' from further distal movement. While the interventional physician needs to apply more force to push the electrode rod 160 to continue moving distally, and may even incorporate a rotation operation while pushing so that the electrode rod 160 can be screwed distally. Thus, in the case where the second pushing rod 140' has been constrained by the restraining piece 111 formed by the insulating layer 110', the electrode rod 160 continues to push the electrode head 120' to the second position, slightly piercing the left bundle branch area M in the myocardium, as shown in FIG. 9*c*. In some embodiments, the restraining piece 111 may be a protrusion formed by the insulating layer 110'.

When removal of the lead 100' is required, the interventional physician may pull the second pushing rod 140' to move proximally to drive the electrode rod 160 and the electrode head 120' to move proximally due to the interference fit of the second pushing rod 140' with the second through hole. At this time, the deformable piece 190 and the anchoring member 130' may also move proximally (the anchoring member 130' moves from the fourth position to the third position). Finally, until the electrode head 120' and the anchoring member 130' are retracted into the insulating layer 110.

Figure 10:
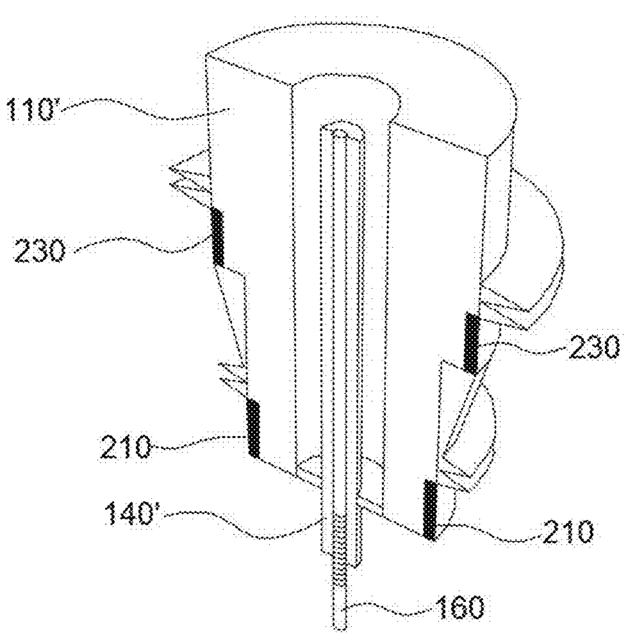
FIG. 10 is a cross-sectional view of a proximal end of the lead of the embodiment shown in FIG. 6.

In some embodiments, as shown in FIG. 10, the proximal end of the second pushing rod 140' continues to proximally extend out of the insulating layer 110', and the proximal end of the electrode rod 160 is provided with graduated markers, such as graduations at a fixed spacing, where the fixed spacing may be 1 mm or other suitable spacing.

In some embodiments, as shown in FIGS. 9*a*, 9*b*, and 9*c*, the insulating layer 110' is formed with a first cathode interface 210, a second cathode interface 220, a first anode interface 230, and a second anode interface 240. The first cathode interface 210 is in communication with the second cathode interface 220 through a cathode conductive coil located inside the insulating layer 110'. The first anode interface 230 is in communication with the second anode interface 240 through an anode conductive coil located inside the insulating layer 110'. It should be noted that when the electrode head 120' of the lead is inserted into the left bundle branch area M in the myocardium, the electrode rod 160 and the second pushing rod 140' extending out of the proximal end of the insulating layer 110' are cut. Then, a pulse generator is connected to the proximal end of the lead. At this time, the pulse generator contacts and is in communication with the first cathode interface 210 and the first anode interface 230 at the proximal end. However, when the electrode head 120' moves distally to contact the left bundle branch area M, the electrode head 120' will contact the second cathode interface 220 located at the distal end of the insulating layer 110'. Meanwhile, since the second anode interface 240 is located outside the lead, the blood outside the lead will communicate the second cathode interface 220 with the second anode interface 240 so that the left bundle branch area M forms a loop with the pulse generator, thereby enabling the pulse generator to deliver electrical pulses to the left bundle branch area M.

It should be noted that the electrode head 120, 120' is energized in various manners and is not limited to the above-mentioned conventional energizing manner. In addition, the energizing position of the electrode head 120, 120' is not limited to the left bundle branch area M, and other regions within the myocardium may be electrically shocked according to different conditions.

Figure 11:
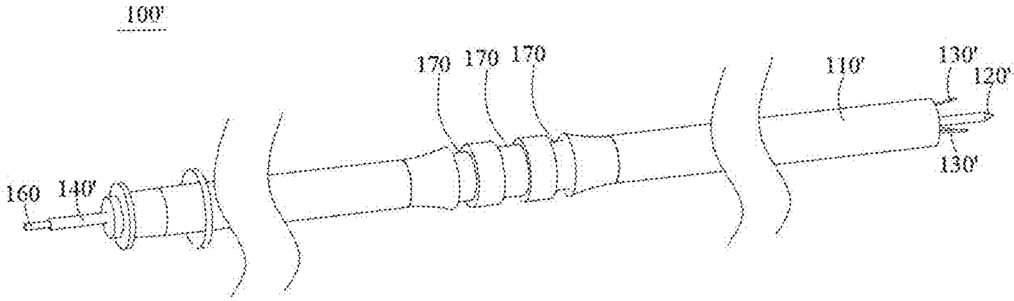
FIG. 11 is a schematic structural diagram of an insulating layer.

FIG. 11 is a side view of an insulating layer 110' arranged with annular grooves 170. Annular grooves 170 formed by recessing inwardly are arranged at a position close to the proximal end of the insulating layer 110' of the lead 100'. In the case where the wire 100' needs to be replaced due to failure or service life, an annular cutting knife cuts the wire 100' at the annular groove 170, thereby exposing the second pushing rod 140', and facilitating the operator to rotate and withdraw the second pushing rod 140' or even the entire lead 100'. In some embodiments, more than one annular groove 170 may be provided. Further, when retracting the second pushing rod 140' or even the entire lead 100', the anchoring member 130' and the electrode head 120' are retracted along a linear path into a corresponding channel of the insulating layer 110' to ensure that they do not continue to insert into the associated (myocardial) tissue of the left bundle branch area M.

It should be noted that the annular groove 170 may also be provided on the insulating layer 110. In some embodiments, annular grooves 170 formed by recessing inwardly are arranged at a position close to the proximal end of the insulating layer 110 of the lead 100.

In some embodiments, although the cross-sectional view shows that the anchoring members 130, 130' are arranged in pairs on two sides of the electrode head 120, 120', in some embodiments, the lead 100, 100' may include three anchoring members 130, 130'. Other numbers of anchoring members 130, 130' are also possible.

The pacing lead of the present application easily enters the left bundle branch area deep in the interventricular septum using a slightly sharp designed pushing rod (the first pushing rod 140 or the second pushing rod 140') and by further rotating the pushing rod, and the operation is simple. According to the graduated markers on the proximal end of the pushing rod, the distal end of the lead is ensured to enter the interventricular septum at a safe and controllable depth, thereby avoiding the perforation of the interventricular septum caused by screwing in too deep. Meanwhile, the anchoring members 130, 130' are used to assist the fixation of the lead to the interventricular septal myocardium, which can ensure the long-term stability of the lead without displacement due to the spontaneous contraction and relaxation of the heart. In addition, the pacing lead 100, 100' of the present application can be in communication with the pulse generator after cutting the electrode rod 160 and the second pushing rod 140' (or the first pushing rod 140) extending out of the insulating layer at the proximal end.

When it is necessary to withdraw the lead, a cutting knife may be used to cut a part of the lead 100, 100' so as to expose the pushing rod, and then the electrode head 120, 120' and the anchoring member 130, 130' may be directly retracted to the inside of the lead 100, 100' by rotating and retracting, thereby completely removing the lead 100, 100' from the body. In the long term, the operation of removing the lead 100, 100' is convenient and has less myocardial damage.

It should be noted that an end close to the lead user is the proximal end, and an end away from the lead user (i.e., close to the heart) is the distal end.

It should be understood that the drawings and specific embodiments described above are only exemplary embodiments of the present application and do not exhaust the possible embodiments of the present application. A person skilled in the art may make various modifications to the above-mentioned specific embodiments within the scope of the present application without departing from the spirit of the present application.

What is claimed is:

1. A lead for pacing, comprising: an insulating layer, an electrode head, at least one anchoring member, a first pushing rod, and a movable portion, wherein the electrode head is movable relative to the insulating layer between a first position and a second position; the at least one anchoring member is movable relative to the insulating layer between a third position and a fourth position, wherein the first position is closer to a proximal end of the lead than the second position; the third position is closer to the proximal end of the lead than the fourth position;

the electrode head in the first position and the at least one anchoring member in the third position are located within the insulating layer; the electrode head in the second position partially or completely extends out of the insulating layer; the at least one anchoring member in the fourth position partially or completely extends out of the insulating layer; a cross section of an electrode extension portion of the electrode head does not increase from a proximal end to a distal end along an axial direction of the electrode head, and a cross section of a member extension portion of each anchoring member of the at least one anchoring member does not increase from a proximal end to a distal end along an axial direction of each anchoring member respectively, wherein the electrode extension portion is a part of the electrode head extending out of the insulating layer, and the member extension portion is a part of the anchoring member extending out of the insulating layer;

the electrode head comprises a first cylindrical portion and a first tapered head connected sequentially from the proximal end to the distal end along the axial direction of the electrode head, or the electrode head is tapered;

the anchoring member comprises a second cylindrical portion and a second tapered head connected sequentially from the proximal end to the distal end along the axial direction of the anchoring member, or the anchoring member is tapered;

wherein the first pushing rod is fixedly connected to the electrode head; the movable portion is formed with a first through hole for the first pushing rod to pass through, and the first pushing rod and the first through hole are in interference connection; the at least one anchoring member is mounted on the movable portion, wherein the movable portion is movably mounted in the insulating layer; wherein when pushing the first pushing rod, the first pushing rod drives the movable portion to move, thereby driving the at least one anchoring member to move.

2. The lead for pacing according to claim 1, wherein when pushing the first pushing rod, the first pushing rod moves distally to drive the electrode head to move from the first position to the second position and drive the at least one anchoring member to move from the third position to the fourth position, the at least one anchoring member extends out of the insulating layer before the electrode head extends out of the insulating layer.

3. The lead for pacing according to claim 1, wherein the insulating layer is arranged with an annular groove formed by recessing inwardly, and the annular groove circumferentially surrounds the insulating layer.

4. The lead for pacing according to claim 3, wherein the at least one anchoring member comprises three anchoring members.

5. The lead for pacing according to claim 1, wherein the insulating layer is formed with a first cathode interface, a second cathode interface, a first anode interface, and a second anode interface, wherein the first cathode interface and the second cathode interface are in communication with each other, and the first anode interface and the second anode interface are in communication with each other.

6. The lead for pacing according to claim 1, wherein the at least one anchoring member is configured to fix the lead for pacing to heart tissue; the at least one anchoring member is configured to be inserted into the heart tissue when the at least one anchoring member is in the fourth position; the at least one anchoring member does not hook the heart tissue when the at least one anchoring member moves from the fourth position to the third position; the electrode head is configured to be inserted into the heart tissue when the electrode head is in the second position; the electrode head does not hook the heart tissue when the electrode head moves from the second position to the first position.

* * * * *